United States Patent
Silberzahn et al.

(10) Patent No.: US 12,063,478 B2
(45) Date of Patent: Aug. 13, 2024

(54) CUSTOM HEARING DEVICE EQUIPPED WITH OPTICAL SENSORS FOR BIOMETRICAL SENSING

(71) Applicant: Sonova AG, Stäfa (CH)

(72) Inventors: Konstantin Silberzahn, Meilen (CH); Markus Leuthold, Stäfa (CH); Markus Müller, Männedorf (CH); Christian Frei-Krumme, Stäfa (CH)

(73) Assignee: SONOVA AG, Stäfa (CH)

( * ) Notice: Subject to any disclaimer, the term of this patent is extended or adjusted under 35 U.S.C. 154(b) by 193 days.

(21) Appl. No.: 17/442,659

(22) PCT Filed: Dec. 18, 2019

(86) PCT No.: PCT/EP2019/086071
§ 371 (c)(1),
(2) Date: Sep. 24, 2021

(87) PCT Pub. No.: WO2020/192956
PCT Pub. Date: Oct. 1, 2020

(65) Prior Publication Data
US 2022/0174432 A1      Jun. 2, 2022

Related U.S. Application Data

(60) Provisional application No. 62/823,888, filed on Mar. 26, 2019.

(51) Int. Cl.
*H04R 25/00* (2006.01)
*A61B 5/00* (2006.01)
*A61B 5/024* (2006.01)

(52) U.S. Cl.
CPC ....... *H04R 25/554* (2013.01); *A61B 5/02427* (2013.01); *A61B 5/02438* (2013.01);
(Continued)

(58) Field of Classification Search
CPC .......... H04R 2225/025; H04R 2225/57; H04R 2225/77; H04R 25/554; H04R 25/652; H04R 25/658
(Continued)

(56) References Cited

U.S. PATENT DOCUMENTS 6,556,852 B1 * 4/2003 Schulze .................. A61B 5/01
600/323
11,543,292 B1 * 1/2023 Ni ......................... A61B 5/7203
(Continued)

FOREIGN PATENT DOCUMENTS

CN            104739422 B      10/2018
EP            3406194 A1 *     11/2018       ......... A61B 5/14552
(Continued)

OTHER PUBLICATIONS

EP 4135346 A2 Method for checking photoplethysmography sensor of hearing device. (Year: 2023).*
(Continued)

*Primary Examiner* — Phylesha Dabney
(74) *Attorney, Agent, or Firm* — Pearne & Gordon LLP

(57) ABSTRACT

A customized in-ear hearing device includes a light source, photodetector, light emission window, and light transmission window. The light source and the photodetector together function as a physiological sensor by emitting light from the light source through the light emission to the skin of a user's ear canal, and detecting at the photodetector light reflected by the skin that passes through the light detection window. The light emission window and light detection window are located at a customized portion of the sidewall of the device that contacts the skin in the ear canal.

27 Claims, 5 Drawing Sheets

(52) U.S. Cl.
CPC ......... *A61B 5/6817* (2013.01); *H04R 25/652* (2013.01); *H04R 25/658* (2013.01); *H04R 2225/025* (2013.01)

(58) Field of Classification Search
USPC ........................................................ 381/315
See application file for complete search history.

(56) References Cited

U.S. PATENT DOCUMENTS

| | | | |
|---|---|---|---|
| 2013/0131519 A1* | 5/2013 | LeBoeuf ................ | A61B 5/681 600/476 |
| 2018/0177416 A1 | 6/2018 | Church et al. | |
| 2020/0178865 A1* | 6/2020 | Trattler .............. | A61B 5/14552 |
| 2021/0100508 A1* | 4/2021 | Vos ...................... | A61B 5/0261 |
| 2021/0298670 A1* | 9/2021 | Roeck ................. | A61B 5/6803 |
| 2022/0071500 A1* | 3/2022 | Boukhayma ....... | A61B 5/02427 |
| 2022/0287639 A1* | 9/2022 | Mostafaei ........... | A61B 5/1455 |

FOREIGN PATENT DOCUMENTS

| | | | | |
|---|---|---|---|---|
| EP | 3623840 A1 * | 3/2020 | ............ | G01S 17/89 |
| EP | 3627856 A1 * | 3/2020 | ......... | A61B 5/02416 |
| EP | 3806495 A1 * | 4/2021 | ......... | A61B 5/02416 |
| EP | 3809725 A2 * | 4/2021 | | |
| EP | 4027658 A1 * | 7/2022 | ......... | A61B 5/02416 |
| EP | 4135346 A2 * | 2/2023 | ......... | A61B 5/02416 |
| WO | 2014092932 A1 | 6/2014 | | |
| WO | WO-2018137771 A1 * | 8/2018 | ............ | F21V 7/0008 |
| WO | WO-2020192956 A1 * | 10/2020 | ........... | A61B 5/0084 |
| WO | WO-2020212483 A1 * | 10/2020 | ......... | A61B 5/02055 |

OTHER PUBLICATIONS

EP 3406194 B1 Circuit arrangement for an optical monitoring system for optical monitoring of a biological parameter (Year: 2018).*
International Search Report for PCT/EP2019/086071 dated Mar. 6, 2020.
Written Opinion for PCT/EP2019/086071 dated Mar. 6, 2020.

* cited by examiner

US 12,063,478 B2

CUSTOM HEARING DEVICE EQUIPPED WITH OPTICAL SENSORS FOR BIOMETRICAL SENSING

BACKGROUND

Some in-ear devices (e.g., hearing aids and ear buds) include optical sensors for detecting physiological data. For example, the devices may include a light source and photodetector to collect photoplethysmogram (PPG) data. In these devices, the light source is used to illuminate tissue inside the ear canal and the photodetector detects the reflected light at the device. Based on the detected light, it is possible to determine changes in light absorption caused by the blood flowing through the tissue during a heartbeat sequence. From this PPG data, physiological information such as heartrate, blood pressure, blood oxygen levels, blood analyte levels, breathing rate or volume, and the like can be determined.

For these devices to properly operate, it is important for the photodetector to be positioned tightly against the skin so that no alien light (e.g., noisy ambient light) is detected. Further it is important for the device to have a well-defined light source to emit a light that can propagate through the skin. In this way, a signal-to-noise ratio can be kept rather low. Problems with the light source and/or the photodetector can decrease the signal-to-noise ratio of the detected physiological data, thus degrading the final signal and causing errors in the determined physiological information. However, current devices are unable to adequately ensure an optimal position and functionality of the light source and photodetector, and thus can suffer from high signal-to-noise ratios and degraded physiological information.

BRIEF SUMMARY OF THE INVENTION

According to an example of the present disclosure, a hearing device comprises a housing shell, at least a portion of the housing shell having a shape that is customized to a shape of a user's ear canal; a light emission window configured to allow transmission of light through a sidewall of the housing shell, the light emission window being in the customized portion of the housing shell; a light detection window configured to allow transmission of light through the sidewall of the housing shell, the light detection window being in the customized portion of the housing shell; a light source configured to emit light from an interior of the housing shell to an exterior of the housing shell through the light emission window, the light source being contained in the housing shell; and a photodetector configured to detect light at the interior of the housing shell from the exterior of the housing shell through the light detection window, the photodetector being contained in the housing shell; and circuitry electrically connected to the light source and the photodetector and configured to control operation of the hearing device, including operation of the light source and the photodetector, the circuitry being contained in the housing shell.

According to another example of the present disclosure, a method of manufacturing a housing shell for a hearing device such that the housing shell has a shape customized to a shape of a user's ear canal comprises determining a user-specific ear canal geometry; providing constraints for positioning at least one of a light emission window and a light detection window on the housing shell, the light emission window and the light detection window configured to allow transmission of light through a sidewall of the housing shell; determining a position for at least one of the light emission window and the light detection window on the housing shell by relating the constraints to said determined user-specific ear canal geometry; and fabricating the housing shell based on said determined ear-canal geometry, wherein at least one of the light emission window and the light detection window is provided at the determined position.

In various embodiments of the above examples, the light source and/or the photodetector are electrically connected to the circuitry via at least one freely movable wire; the hearing device further comprises a printed circuit board (PCB), wherein the light source and the photodetector are mounted on opposing sides of the PCB; the customized portion of the housing shell comprises a surface indentation and/or a through hole, and the light source or the photodetector is positioned at the indentation or in the through hole; the hearing device further comprises a waveguide optically coupling the light source to the light emission window or optically coupling the photodetector to the light detection window, the waveguide extending at least partially through the sidewall of the customized portion of the housing shell; the light emission window and the light detection window are each located at least 1 mm from the edge of the customized portion of the housing shell; the light source and/or the photodetector are mounted to a faceplate of the hearing device; at least a portion of the housing shell is made of a material transparent to wavelengths of light emitted by the light source; the light source and the photodetector constitute a photoplethysmography sensor; and/or the light source is a light emitting diode; at least one of the light emission window and the light detection window is located at a sealing zone of the housing shell; the light emission window and the light detection window are provided at a distance; the distance comprises a distance in an axial direction and/or in a circumferential direction of the housing shell.

DETAILED DESCRIPTION

Figure 1:
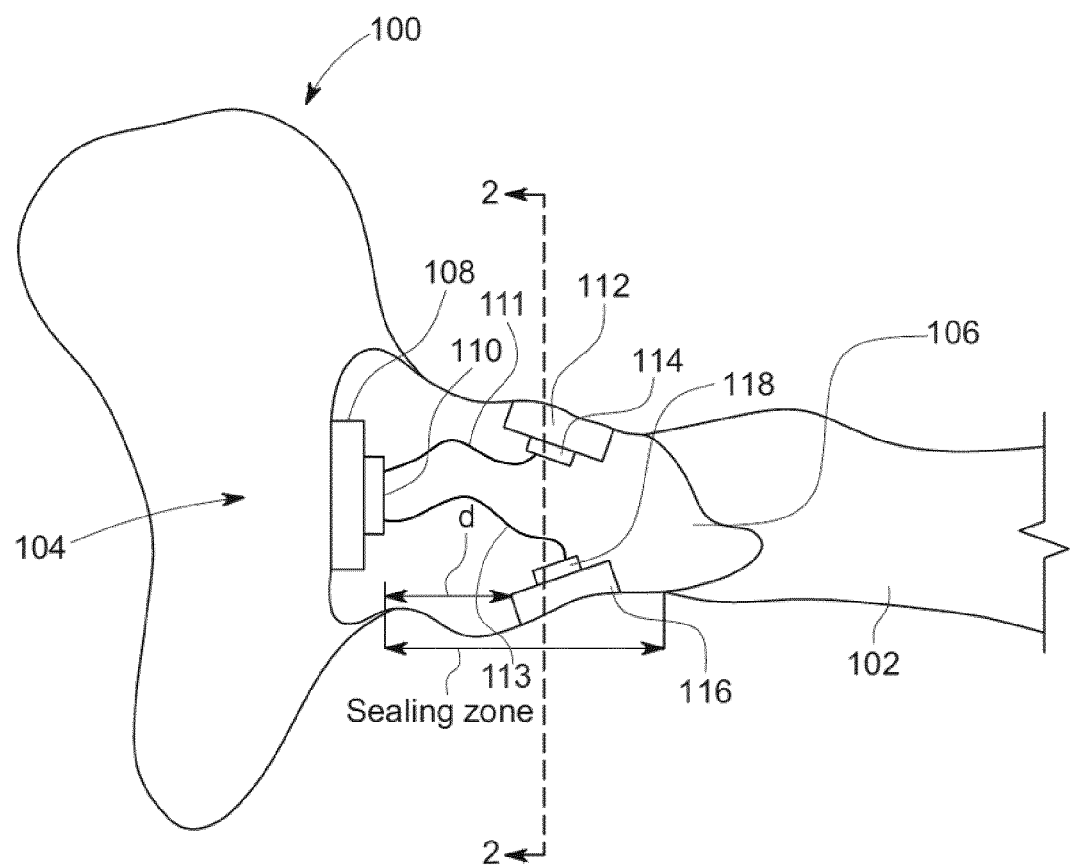
FIG. 1 is a first example in-ear device according to the present disclosure.

In view of the above, the present disclosure relates to in-ear devices capable of optical physiological measurements that overcome the deficiencies of such current devices. In particular, the disclosure relates to custom hearing devices comprising a housing shell configured to be at least partially inserted into an ear canal, where the housing shell is individually customized to the shape of the ear canal, capable of measuring photoplethysmogram (PPG) data. These hearing devices may be referred to as in-the-ear (ITE), completely-in-the-ear canal (CIC) devices (e.g., as with hearing aids), which are entirely inserted into the ear canal, and/or receiver-in-the-ear canal (MC) or behind-the-ear (BTE) devices (e.g., as with hearing aids) that have an external part worn behind the ear in addition to the portion located inside the ear.

According to conventional techniques for making custom shells, ear molds, ear pieces, and the like, a user-specific ear canal geometry is first determined. This may particularly include taking an ear impression and then 3D scanning the impression. A 3D model of the impression may then be created by in part detailing where the shape of the final shell is fit into an dataset of the 3D scan of the impression (e.g., with 3D modeling software). The custom shell is then manufactured, for example by additive manufacturing techniques. Finally, the device is assembled. Typically, custom shells have a lateral opening on which a faceplate or accessory is attached to cover the lateral opening. Electronic components of the hearing device can be attached to the faceplate/module and/or provided inside an inner volume enclosed by the housing. For example, a printed circuit board (PCB) including the electronic components can be provided inside the inner volume. Thus, the final assembly includes inserting the electronic components into an inner volume of the shell and covering a lateral opening of the shell with the faceplate attached to the shell.

For custom in-ear devices having optical sensors, the standard materials (e.g., acrylate for additive manufacturing) used to manufacture the shells are not transparent for the wavelengths of light used in those sensors. Thus, the sensors are generally placed at the outside of the custom shell, but this limits the degree of freedom in the modelling and custom design of the shell. Furthermore, the locations of these sensors may be patient specific, thereby further increasing manufacturing complexity and cost.

According to the present disclosure, the creation of the 3D model described above further includes determining a set of constraints for an optimal position of a light emission window (optically connected to a light source) and a light detection window (optically connected to a photodetector) in the custom shell. These constraints may include locations that constrain light emission and detection, a minimal/maximal distance between the light source and photodetector, and the like. The light emission and detection windows allow passage of light through the custom shell for emission to the exterior of the in-ear device by the light source, and detection in the interior of the in-ear device by the photodetector.

An example in-ear device 104 according to the present disclosure is illustrated in FIG. 1. As seen therein, the in-ear device 104 having a shell housing 106 is located in an ear canal 102 of an ear 100. As noted above, the in-ear device 104 includes a faceplate 108 covering a lateral opening of the shell 106, and to which circuitry 110, in particular a PCB and/or other electronic components, may be mounted. Although not shown, controls/interface elements (e.g., buttons or switches) may be attached to the outside of the faceplate and coupled with the electronic components 110 for user interaction with the device 104. Additionally, a light emission window 112 and light source 114 (e.g., an LED), and a light detection window 116 and photodetector 118 (e.g., a photodiode) are included with the in-ear device 104.

In particular, the light emission window 112 is preferably located in the sealing zone of the in-ear device 104 (a portion of the shell 106 that is in contact with the ear canal 102, indicated in FIG. 1) such that no light dissipates to either free field or the residual volume. The sealing zone portion of the in-ear device 104 is preferably customized to the shape of the user's ear canal 102, thereby maximizing possible contact between the in-ear device 104 and the skin of the ear canal 102. A minimal distance d (indicated in FIG. 1) between the light emission window 112 and the inner and outer extreme points of the sealing zone may also be determined, the minimal distance d being the minimal distance needed so that substantially no light is emitted outside the sealing zone. For example, the minimal distance can be at least 1 mm. Similarly, the light detection window 116 is preferably located in the sealing zone such that no external ambient light is received by the photodetector 118. A minimal distance d between the light detection window 116 and the inner and outer extreme points of the sealing zone may again be determined so that substantially all the detected light is received from the sealing zone. Again, for example, the minimal distance can be at least 1 mm.

Figure 2:
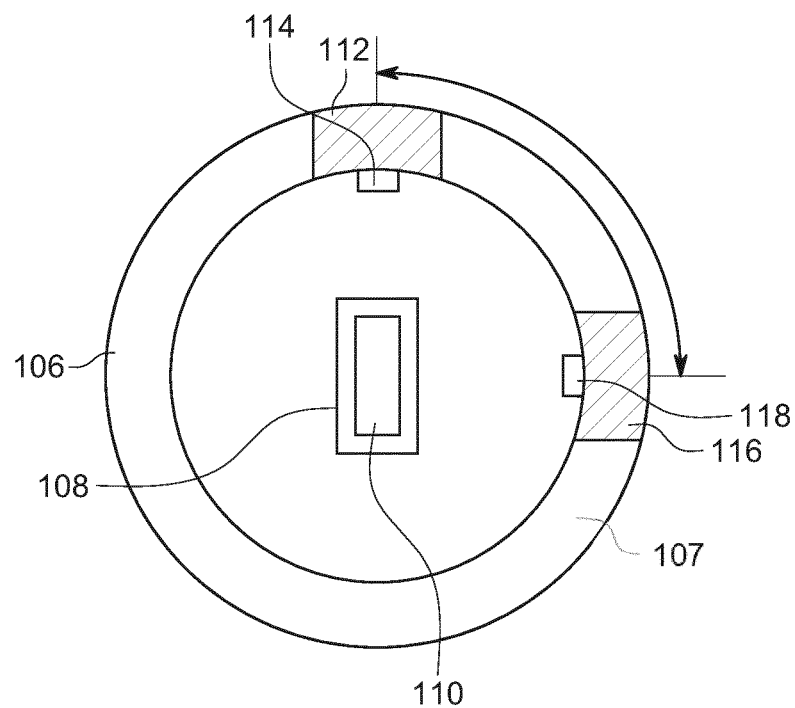
FIG. 2 is a cross-section of the example in-ear device of FIG. 1.

A cross-section of the in-ear device 104 of FIG. 1, taken along the line shown in FIG. 1, is illustrated in FIG. 2. As seen therein, the light emission window 112 and the light detection window 116 are provided in the shell housing 106, in particular in a sidewall 107 of the shell housing 106. The light emission window 112 and the light detection window 116 extend through the sidewall 107. The sidewall 107 may enclose the interior of the shell housing 106, at least within the customized portion of the shell housing 106. The sidewall 107 may be customized to an individual shape of the ear canal 102, at least within the customized portion of the shell housing 106. An inner surface of the sidewall 107 may be oriented toward the interior of the shell housing 106. An outer surface of the sidewall 107 may be at least partially comprise the sealing zone of the shell 106. The outer surface may at least partially be oriented toward the ear canal when the shell 106 is inserted into the ear canal. A minimal and/or maximal distance L between the light emission window 112 and the light detection window 116 may also be determined as a constraint. The distance can comprise a distance L in a circumferential direction of shell housing 106, as illustrated, which is subsequently referred to as a circumferential distance. The distance can comprise a distance in an axial direction of shell housing 106, wherein the axis of shell housing 106 extends between faceplate 108 and a rear end of shell housing 106 opposing faceplate 108, subsequently referred to as an axial distance. Preferably, the minimal distance is one that allows separation of the emitted light from the detected light so that light at the photodetector 118 is not directly received from the light source 114 (e.g., as a bleed), but rather is received from the skin of the ear canal 102. In some embodiments, the light emission window 112 and light detection window 116 can be provided at substantially adjacent areas, for instance when a light beam emitted from the light source 114 is directed away from the neighboring area at which the light detection window 116 is provided. In some embodiments, the minimal distance can be at least 1 mm. In some embodiments, the minimal distance comprises a circumferential distance L corresponding to at least one fourth of a total circumference of shell housing 106. In some embodiments, the minimal distance comprises an axial distance corresponding to at least one tenth, more preferred at least one fifth, of a total length of shell housing 106 in the axial direction. In some embodiments, the light emission window 112 and light detection window 116 can be provided at substantially opposing areas of a circumference of the shell 106 and/or at two longitudinally opposing ends of the shell to maximize the distance L.

From the determined set of constraints, the light emission window 112 and the light detection window 116 can then be manufactured with the shell 106 at locations corresponding to the determined constraints. The windows 112, 116 may be formed directly during an additive manufacturing process (e.g., by omitting addition of material at the corresponding locations), or by drilling holes into walls of the manufactured shell 106 at the corresponding locations. The light source (e.g., an LED) and/or the photodetector can then be inserted into the windowed opening of the shell 106. In some embodiments, the light emission window 112 and the light detection window 116 could also be embodied as a light transparent surface of the custom shell, for instance by covering the holes with an acrylic lacquer.

Figure 3:
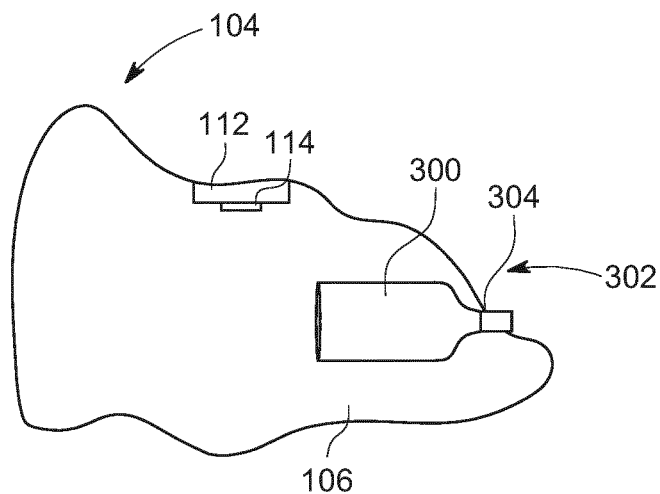
FIG. 3 is a second example in-ear device of the present disclosure.

In other embodiments only the light emission window or the light detection window is fabricated on the shell in the manner described above. In these embodiments, the other of the light emission window and the light detection window is attached to a tip/end of the shell, together with the corresponding light source or photodetector, as a fitment to the in-ear device. The fitment can further comprise a receiver hole, a wax guard, and/or a receiver, or the like. An example of such an embodiment is shown in FIG. 3. There, the light emission window 112 and light source 114 are shown in the same form as in FIG. 1; however, the light detection window and photodetector are embodied as the fitment 300 attached at an end 302 of the shell 106. As shown in the example of FIG. 3, the fitment 300 is provided through a receiver hole 304 at the end of 302 of the shell 106.

In some embodiments, the light source and the photodetector may be positioned substantially at the locations of the light emission window and light detection window, respectively, as shown for example in the embodiment illustrated in FIG. 1. However, the light source and photodetector may instead be positioned elsewhere in or on the shell 106, remote from the windows 112, 116. In these embodiments, light from the light source 114 is transmitted to the light emission window 112, and from the light detection window 116 to the photodetector 118, via waveguides or similar optical couplings.

Figure 4:
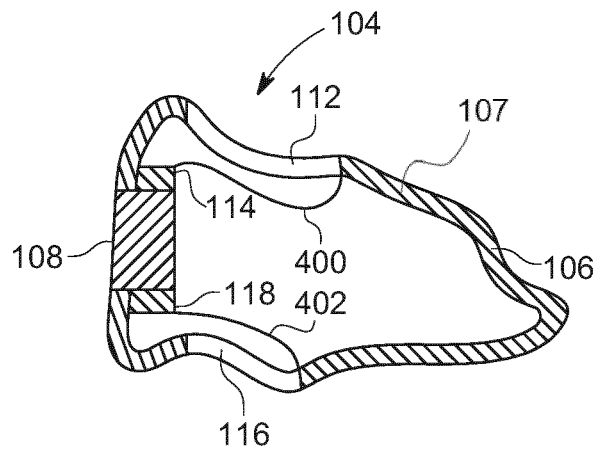
FIG. 4 is a third example in-ear device of the present disclosure.

According to the example embodiment illustrated in FIG. 4, the light source 114 and photodetector 118 may be mounted to a standard face plate 108 in a fixed position such that the light is emitted from the light source 114 and detected by the photodetector 118 in a sideways direction toward the inner walls of the shell 106. Waveguides 400, 402 optically connect the light source 114 and the photodetector 118 to the light emission window 112 and the light detection window 116, respectively. The waveguides 400, 402 may be integrated in the sidewall 107 of the shell 106, run along an inner surface of the sidewall 107 of the shell 106, or be freely moveable inside the shell 106 such that the light emitted from the light source 114 enters the waveguide 400 (e.g., at the sidewall of the shell 106) and is directed to the light emission window 112 by the waveguide 400; and light is received at the light detection window 116 and directed to the photodetector 118 by the waveguide 402 such that the received light leaving the waveguide 402 can be further received by the photodetector 118. The active areas of each device (where light is emitted from the light source 114, and detected by the photodetector 118) may simply face waveguide openings in the interior of the shell 106, or the light source 114 and photodetector 118 may be attached such that the active areas abut the openings of the waveguides 400, 402 (or directly attached to the waveguides 400, 402), thereby reducing excess light noise and bleeding.

Figure 5:
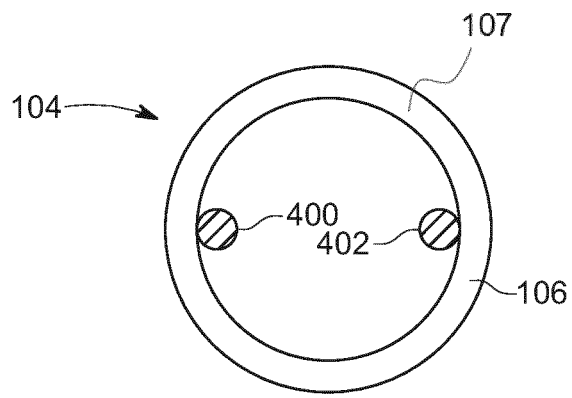
FIG. 5 is a cross-section of an in-ear device illustrating a first example waveguide configuration within the in-ear device.

Such waveguides can be designed and manufactured as follows. According to a first example illustrated in FIG. 5 (showing a cross-section of an in-ear device 104), a tube or canal corresponding to the waveguide 400, 402 may be printed along the inner wall of the shell 106 or through the volume, in a manner similar to the manufacturing of a vent-tube. This may include forming the tube by additive manufacturing, whereby additional material is printed on an inner surface of the shell 106 to form the tube). As noted above, in some embodiments the medial end of the tube (the opening of the waveguide 400, 402 facing the light source 114 or photodetector 118, or facing into the interior of the shell 106) is designed to tightly connect to the light source 114 or photodetector 118 to reduce noise and bleeding. The other end of the tube thus opens to the light emission or detection window 112, 116. A light guiding liquid material (e.g. transparent silicone or acrylate or epoxy) can then be injected in the tube and cured. Alternatively, glass fibers can be inserted into the empty tube. Such a design has the advantage of being customized and cost effective.

Figure 6:
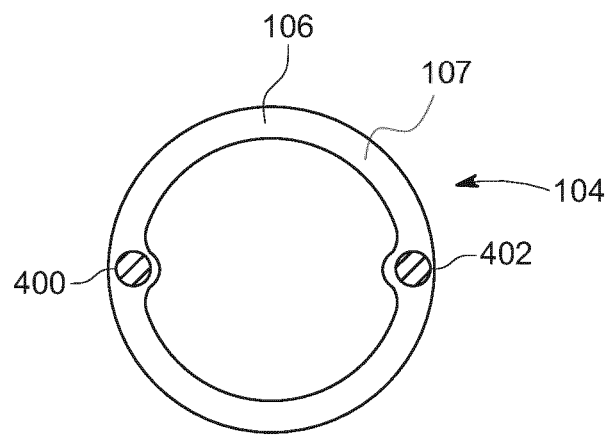
FIG. 6 is a cross-section of an in-ear device illustrating a second example waveguide configuration within the in-ear device.

In another example, the waveguides may be manufactured with a two-component 3D-printing technology to fully integrate the waveguides 400, 402 into in the wall of the shell 106, as seen in the in-ear device 104 cross-section illustrated in FIG. 6. With this process, the light transparent waveguide 400, 402 and the opaque shell material are printed simultaneously in the same process step. The waveguide 400, 402 may also be manufactured by leaving a cavity in the wall during the additive manufacturing process (e.g., whereby no shell material is printed in the region corresponding to the tube), or by extrusion after forming the shell 106.

Figure 7:
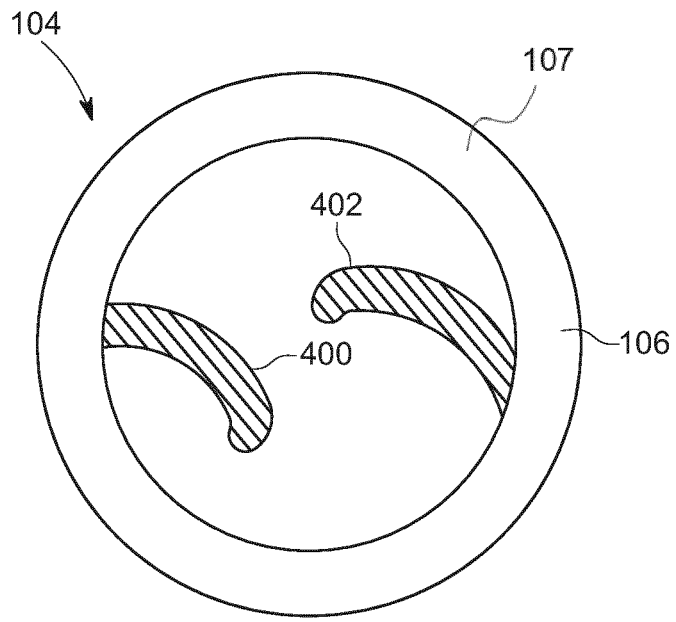
FIG. 7 is a cross-section of an in-ear device illustrating a third example waveguide configuration within the in-ear device.

In still another example, as seen in the in-ear device 104 cross-section illustrated in FIG. 7, the waveguide 400, 402 is rigid or flexible light guide (e.g., made of silicone, glass fibers, and the like), in contact with and attached to the light source 114 or photodetector 118, and is freely guided through the in-ear device towards the window 112, 116 at the shell 106. The shell 106 may contain a through hole between the appropriate window and medial opening to the inside of the shell 106, and through which the light guide can be inserted.

Of course, the waveguides 400, 402 of an individual in-ear device may be manufactured according to different techniques. It is also envisioned that an individual in-ear device may employ a waveguide for only one of the light source 114 or photodetector 116, or different embodiments of the waveguides for each of the light source 114 and photodetector 116.

In still other embodiments, the shell 106 itself may be of a material that is transparent for the specific wavelength of the light source 114 and photodetector 118. In these cases, the entire shell 106, only the sealing zone, or only a portion of the sealing zone corresponding to the light emission and detection windows 112, 116/light source 114 and photodetector 118, may be of the transparent material. In this manner, the light emission and detection windows 112, 116 are constituted by the transparent portions of the shell.

Figure 8:
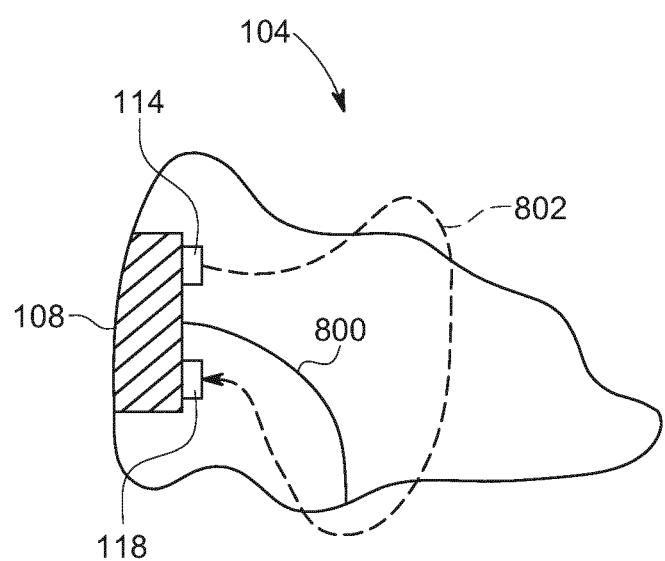
FIG. 8 is a fourth example in-ear device of the present disclosure.
Figure 9:
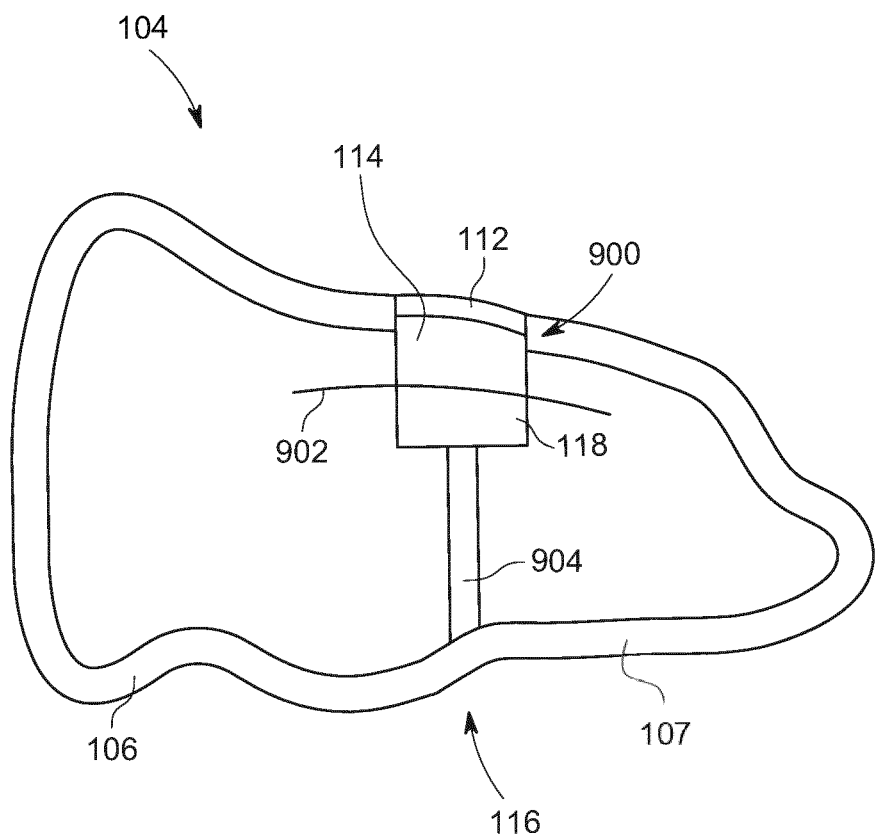
FIG. 9 is a fifth example in-ear device of the present disclosure.

An example of such an embodiment is illustrated in FIG. 8. Therein, the light source 114 and photodetector 118 may be mounted to the inner side of the face plate 108. In order to prevent a short cut between the light source 114 and photodetector (so that the photodetector does not detect light directly emitted by the light source without first passing through the skin), the light source 114 may be separated from the photodetector 118 within the shell 106 by a partition wall 800. The partition wall 800 thus forces the photodetector 118 to detect light 802 that leaves the shell 106, travels through the skin, and then is reflected back into (and reenters the shell 106) on an opposing side of the partition wall 800. The wall 800 may be printed from the same material as the shell 106. As the shell material is transparent to the light, the partition wall 800 can be made opaque by applying an opaque lacquer in a subsequent manufacturing step. Alternatively, the partition wall 800 may be made by using a 2-component 3D-printing technology using an opaque material, or the like. Where only a portion of the shell 106 is transparent, the transparent portion of the shell 106 can be produced by using 2-component 3D-printing, or by making the entire shell 106 transparent and then selectively apply an opaque lacquer to the transparent shell 106 where light should be blocked (the regions not corresponding to the windows).

Where all or a portion of the shell is transparent as described above, the light source 114 and the photodetector 118 may also be located near an inner wall of the shell, for example, at the sealing zone instead of being mounted on the face plate. Such an embodiment is illustrated in the example in-ear device 104 of FIG. 9. When located at the shell 106 wall as shown in FIG. 9, the shell may have an indentation or a through hole 900 at the sealing zone in which the light source 114 may be positioned. The light emission window 112 is thus provided at the indentation or through hole 900. The indentation or through hole 900 can be coated, in particular between the sidewalls of the indentation or through hole 900 provided in the sidewall 107 of the shell 106, with an opaque lacquer to seal and allow transmission of light. Although not shown in FIG. 9, the photodetector 118 may also or instead be positioned at a through hole of the shell 106 in a similar manner.

In some instances, the light source 114 and the photodetector 118 are mounted on opposing faces of a PCB stripe 902, the photodetector 118 being on the side of the PCB 902 opposing the indentation or through hole 900. In this way, light emitted from the light source 114 can be isolated from the light detected by the photodetector 118 by the PCB 902. Positioning the light source 114 in the indentation or through hole 900 further helps prevent a light short between the light source 114 and photodetector 118 by ensuring substantially all of the light emitted by the light source 114 is directed out of the shell 106, rather than illuminating an interior of the shell 106. As noted above, where the photodetector 118 is positioned in an indentation or through hole (and thus allowed to only capture light entering through a light detection window) and mounted to one side of a PCB, the light source 114 would thus be mounted on an opposing side of the PCB.

For the element not positioned in the indentation or through hole 900 (the photodetector 118 in FIG. 9), a waveguide 904 may be further provided as an optical connection between that element and the corresponding window (or portion of the shell 106 constituting a window). For example, where the light source 114 is in the indentation or through hole 900 and the photodetector 118 is on an opposing side of the PCB 902, a waveguide 904 may optically connect the photodetector 118 to the portion of the shell acting as a light detection window 116. Similarly, where the photodetector is in the indentation or through hole and the light source is on an opposing side of the PCB, a waveguide may optically connect the light source to the portion of the shell acting as a light emission window.

For each of the above embodiments, the light source 114 and the photodetector 118 are electronically connected to sensor processing circuitry, which may include a processor, discrete circuit components, and the like. Any or all of the circuitry elements may be integrated as part of an integrated semiconductor device and/or may be mounted on a printed circuit board. The printed circuit board and associated circuitry may mounted to or integrated with the faceplate 108 with or in addition to circuitry 110 shown in FIG. 1, attached as a fitment of the shell (e.g., as with fitment 300 shown in FIG. 3), or be positioned inside the cell (e.g., as with the PCB 902 of FIG. 9). The circuitry may also be integrated with or separate from other processing circuitry of the in-ear device, such as the circuitry 110 shown in FIG. 1. The light source 114 and photodetector 118 may be connected to any corresponding circuitry in various ways. For example, in some embodiments, the light source 114 and/or the photodetector 118 may be mounted directly to a printed circuit board (e.g., as the circuitry 110 on faceplate 108 shown in FIG. 1, or on PCB 902 shown in FIG. 9). In these cases, the light source 114 and the photodetector 118 may be on the same, or opposing sides, of the same printed circuit board, or on different printed circuit boards. If not mounted to a printed circuit board, or otherwise remote from the circuitry, the light source and/or the photodetector may be electrically connected to any of the circuitry by wires 111, 113. The wires may be, for example, free moving litz wires. The use of litz wires provides mechanical freedom in the assembly of the in-ear device.

While various features and embodiments are presented above, it should be understood that the features and embodiments may be used singly or in any combination thereof. Further, it should be understood that variations and modifications may occur to those skilled in the art.

What is claimed is:

1. A hearing device comprising:
   a housing shell, at least a portion of the housing shell having a shape that is customized to a shape of a user's ear canal;
   a light emission window configured to allow transmission of light through a sidewall of the housing shell, the light emission window being a window through the customized portion of the housing shell;
   a light detection window configured to allow transmission of light through the sidewall of the housing shell, the light detection window being a window through the customized portion of the housing shell;
   a light source configured to emit light from an interior of the housing shell to an exterior of the housing shell through the light emission window, the light source being at least partially contained in the housing shell;
   a photodetector configured to detect light at the interior of the housing shell from the exterior of the housing shell through the light detection window, the photodetector being at least partially contained in the housing shell; and
   circuitry contained in the housing shell and electrically connected to the light source and the photodetector and configured to control operation of the hearing device, including operation of the light source and the photodetector,
   wherein the light source and/or the photodetector are mounted to a faceplate of the hearing device.

2. The hearing device of claim 1, wherein the light source and/or the photodetector are electrically connected to the circuitry via at least one freely movable wire.

3. The hearing device of claim 1, further comprising a printed circuit board (PCB), wherein the light source and the photodetector are mounted on opposing sides of the PCB.

4. The hearing device of claim 1, wherein the customized portion of the housing shell comprises a surface indentation and/or a through hole, and the light source or the photodetector is positioned at the indentation or in the through hole.

5. The hearing device of claim 1, further comprising a waveguide optically coupling the light source to the light emission window or optically coupling the photodetector to the light detection window, the waveguide extending at least partially within the sidewall of the customized portion of the housing shell.

6. The hearing device of claim 1, wherein the light source is a light emitting diode.

7. The hearing device of claim 1, wherein the light source and the photodetector constitute a photoplethysmography sensor.

8. A hearing device comprising:
a housing shell, at least a portion of the housing shell having a shape that is customized to a shape of a user's ear canal;
a light emission window configured to allow transmission of light through a sidewall of the housing shell, the light emission window being a window through the customized portion of the housing shell;
a light detection window configured to allow transmission of light through the sidewall of the housing shell, the light detection window being a window through the customized portion of the housing shell;
a light source configured to emit light from an interior of the housing shell to an exterior of the housing shell through the light emission window, the light source being at least partially contained in the housing shell;
a photodetector configured to detect light at the interior of the housing shell from the exterior of the housing shell through the light detection window, the photodetector being at least partially contained in the housing shell; and
circuitry contained in the housing shell and electrically connected to the light source and the photodetector and configured to control operation of the hearing device, including operation of the light source and the photodetector,
wherein the light emission window and the light detection window are each located at least 1 mm from an edge of the customized portion of the housing shell.

9. The hearing device of claim 1, wherein at least a portion of the housing shell corresponding to the light emission window or the light detection window is made of a material transparent to wavelengths of light emitted by the light source.

10. The hearing device of claim 8, wherein the light source and/or the photodetector are electrically connected to the circuitry via at least one freely movable wire.

11. The hearing device of claim 8, further comprising a printed circuit board (PCB), wherein the light source and the photodetector are mounted on opposing sides of the PCB.

12. The hearing device of claim 8, wherein the customized portion of the housing shell comprises a surface indentation and/or a through hole, and the light source or the photodetector is positioned at the indentation or in the through hole.

13. The hearing device of claim 8, further comprising a waveguide optically coupling the light source to the light emission window or optically coupling the photodetector to the light detection window, the waveguide extending at least partially within the sidewall of the customized portion of the housing shell.

14. The hearing device of claim 8, wherein at least a portion of the housing shell corresponding to the light emission window or the light detection window is made of a material transparent to wavelengths of light emitted by the light source.

15. The hearing device of claim 8, wherein the light emission window and the light detection window are provided at a circumferential distance about the housing shell of at least one fourth of a total circumference of the housing shell.

16. The hearing device of claim 8, wherein the light source is a light emitting diode.

17. The hearing device of claim 8, wherein the light source and the photodetector constitute a photoplethysmography sensor.

18. A hearing device comprising:
a housing shell, at least a portion of the housing shell having a shape that is customized to a shape of a user's ear canal;
a light emission window configured to allow transmission of light through a sidewall of the housing shell, the light emission window being a window through the customized portion of the housing shell;
a light detection window configured to allow transmission of light through the sidewall of the housing shell, the light detection window being a window through the customized portion of the housing shell;
a light source configured to emit light from an interior of the housing shell to an exterior of the housing shell through the light emission window, the light source being at least partially contained in the housing shell;
a photodetector configured to detect light at the interior of the housing shell from the exterior of the housing shell through the light detection window, the photodetector being at least partially contained in the housing shell; and
circuitry contained in the housing shell and electrically connected to the light source and the photodetector and configured to control operation of the hearing device, including operation of the light source and the photodetector,
wherein the light emission window or the light detection window is located at a sealing zone of the housing shell, the sealing zone defined as a portion of the housing shell that is contact with the ear canal when the housing shell is inserted into the ear canal.

19. The hearing device of claim 18, wherein the light source and/or the photodetector are electrically connected to the circuitry via at least one freely movable wire.

20. The hearing device of claim 18, further comprising a printed circuit board (PCB), wherein the light source and the photodetector are mounted on opposing sides of the PCB.

21. The hearing device of claim 18, wherein the customized portion of the housing shell comprises a surface indentation and/or a through hole, and the light source or the photodetector is positioned at the indentation or in the through hole.

22. The hearing device of claim 18, further comprising a waveguide optically coupling the light source to the light emission window or optically coupling the photodetector to the light detection window, the waveguide extending at least partially within the sidewall of the customized portion of the housing shell.

23. The hearing device of claim 18, wherein at least a portion of the housing shell corresponding to the light emission window or the light detection window is made of a material transparent to wavelengths of light emitted by the light source.

24. The hearing device of claim 18, wherein the light emission window and the light detection window are provided at a circumferential distance about the housing shell of at least one fourth of a total circumference of the housing shell.

25. The hearing device of claim 18, wherein the light source is a light emitting diode.

26. The hearing device of claim 18, wherein the light source and the photodetector constitute a photoplethysmography sensor.

27. A hearing device comprising:
- a housing shell, at least a portion of the housing shell having a shape that is customized to a shape of a user's ear canal;
- a light emission window configured to allow transmission of light through a sidewall of the housing shell, the light emission window being a window through the customized portion of the housing shell;
- a light detection window configured to allow transmission of light through the sidewall of the housing shell, the light detection window being a window through the customized portion of the housing shell;
- a light source configured to emit light from an interior of the housing shell to an exterior of the housing shell through the light emission window, the light source being at least partially contained in the housing shell;
- a photodetector configured to detect light at the interior of the housing shell from the exterior of the housing shell through the light detection window, the photodetector being at least partially contained in the housing shell; and
- circuitry contained in the housing shell and electrically connected to the light source and the photodetector and configured to control operation of the hearing device, including operation of the light source and the photodetector,
- wherein the light emission window and the light detection window are provided at a circumferential distance about the housing shell of at least one fourth of a total circumference of the housing shell.

* * * * *